United States Patent [19]

Schramm

[11] Patent Number: 4,925,629
[45] Date of Patent: May 15, 1990

[54] DIAGNOSTIC DEVICE

[75] Inventor: Willfried Schramm, Ann Arbor, Mich.

[73] Assignee: BioQuant, Inc., Ann Arbor, Mich.

[21] Appl. No.: 225,194

[22] Filed: Jul. 28, 1988

[51] Int. Cl.⁵ .............................................. G01N 30/00
[52] U.S. Cl. ................................. 422/82.05; 422/100; 422/102; 422/65; 422/82.08; 436/8
[58] Field of Search .................. 422/68, 100, 102, 104, 422/64, 65, 73; 436/8, 14, 15, 16

[56] References Cited

U.S. PATENT DOCUMENTS

| | | | |
|---|---|---|---|
| 4,058,370 | 11/1977 | Souvaniemi | 422/100 |
| 4,265,855 | 5/1981 | Mandle et al. | 422/65 |
| 4,345,843 | 8/1982 | Berglund et al. | 422/64 |
| 4,383,041 | 5/1983 | Kutsusawa et al. | 422/65 |
| 4,554,839 | 11/1985 | Hewett et al. | 422/65 |
| 4,681,742 | 7/1987 | Johnson et al. | 422/65 |

Primary Examiner—Barry S. Richman
Assistant Examiner—Gregory R. Muir
Attorney, Agent, or Firm—Reising, Ethington, Barnard, Perry & Milton

[57] ABSTRACT

A diagnostic device (10) includes a plurality of standard solutions for being dispensed into a row of wells (20), the standard solutions contained within a predetermined number of standard tubes which are spaced a predetermined distance apart equal to the distance between the plurality of wells (20) whereby a single pipettor (28) can transfer the standards from the entire row of standard tubes (26) to a single row of wells (20) in a single transfer step. The invention further provides a mixing mechanism for agitating the entirety of a microtiter plate seated thereover.

10 Claims, 2 Drawing Sheets

DIAGNOSTIC DEVICE

TECHNICAL FIELD

The present invention relates to a diagnostic device for assaying unknown constituent concentrations of a sample. More specifically, the present invention relates to a diagnostic kit used for immunoassay determinations of constituents such as hormones in a blood sample.

BACKGROUND ART

It is desirable to make efficient and qualitatively accurate determinations of microscopic amounts of constituents of samples, such as the determination of analytes including hormones, enzymes, metabolites, and drugs in a sample of blood or other fluid. Immunoassay techniques have been used for such determinations.

Immunoassay (IA) is the generic term for systems of quantitative in vitro measurement based on the principal of saturation analysis, displacement analysis, or competitive analyte binding. Since such techniques are extremely sensitive and very specific. IA techniques are used for the determination of physiologically, pharmocologically or forensically important analytes in biological fluids.

One of the techniques in IA is derived from the observation that unlabeled analyte displaces labeled analyte from an antibody that can bind the analyte. With an antibody concentration and the labeled analyte held constant, the binding of the label is quantitatively related to the amount of unlabeled analyte that is added. Thus, known analyte standards can be used initially to prepare a plot of the fraction of bound radioactive analyte against the concentration of added non-labeled analyte.

In operation, the method of heterogeneous immunoassays requires the separation of a labeled analyte of interest into bound and unbound fractions after its interaction with an antibody in the presence of an unknown quantity of unlabeled analyte. Homogeneous assays that do not require a separation step are becoming increasingly popular.

Various devices are used in IA techniques. Occasionally, a microtiter plate is used, the microtiter plate being a plastic plate including a plurality of rows of wells for containing the sample solutions. For example, an antibody can be bound to the walls of the wells. In radioimmunoassays (RIA), a derivative of the analyte which is radioactively labeled is used as signal generator for quantitative measurements of analyte. A sample or standard and radiolabeled analyte (tracer) are added to the wells The constituents of the wells are agitated during incubation and the liquid of the wells is removed. The wells are then separated and placed in a radioactivity counter to determine radioactive binding. Alternatively, the analyte can be labeled with non-radioactive substances including enzymes and substances emitting fluorescence or luminescence. In addition, the label can be on a second binding substance that binds to the analyte that is already bound to the wall of the well.

Several problems have been uncovered utilizing the aforementioned technique. Standards of the substance to be measured are prepared prior to assaying samples of unknown substance concentration from a stock solution of substance by serial dilutions. These dilutions are then distributed to the designated wells or other containers which are then subjected to the assay procedure. From an obtained physical measurement (e.g. radioactivity), a standard curve is eventually constructed which represents the mathematical or graphical function (standard curve of the concentration of the substance in the standards, that being the known parameter) against the physical measurements of the unknown samples. The standard curve is then used to extrapolate from a physical measurement in a sample of unknown substance concentrations to the concentration predicted by the standard curve.

The disadvantage of this prior art technique involves the preparation of serial dilutions for the standards prior to assaying. This is inefficient because it is time consuming and can introduce inaccuracies by the operator. Each serial dilution allows for a first inaccuracy to be developed and each following serial dilution perpetuates and sometimes accentuates the inaccuracy. Therefore, there are prior art techniques utilizing predispensed standards. However, these standards are distributed such that each standard solution needs to be delivered to the assay well separately with a single pipettor.

A second concern is an efficient means for mixing the contents of each of the wells during the incubation step of the procedure. Care must be taken to not spill the contents of each well yet sufficient agitation must be made in order to properly mix the contents of each well.

Another concern during the processing of the samples of the microtiter plates is that some manufacturers manufacture trays comprising unitary rows of wells interconnected together, each row being connected at its end to a surrounding base of the plate. Once several rows are removed from the plate, it is possible to confuse the order of the rows and thereby lose the identity of tested samples.

The present invention provides an efficient means for providing for transfer a plurality of known concentration standards so that the standards can be transferred in a single step. The present invention further provides an effective and efficient means for agitating the wells containing the standards and samples. The present invention further provides a means of identifying the proper location of a row of wells which has been displaced from the microtiter plate to avoid loss of identity of the row. Finally, the present invention provides a single kit within a single housing incorporating the aforementioned inventions into a unitary kit providing all of the means necessary to conduct an IA incubation procedure.

SUMMARY OF THE INVENTION

In accordance with the present invention, there is provided a diagnostic device for assaying unknown constituent concentrations of a sample, the device including the combination of housing means for containing the device and tube means disposed within the housing means. The tube means includes a plurality of rows of wells for receiving and containing a sample including the constituent to be assayed. Each row includes a predetermined number of wells or tubes. Standard means is disposed within the housing means and contains a plurality of standard solutions for being dispensed into a row of the wells or tubes. The standard means includes the predetermined number of standard tubes, each of the tubes containing a known concentration of the constituent and each of the tubes being spaced the predetermined distance apart equal to the spacing of the wells in each of the rows whereby a single pipettor can transfer the standard from the entire row of standard tubes to a single row of the wells in a single transfer step. Mixing means are disposed within the housing means and below the tube means for agitating the wells and mixing the samples contained therein. The mixing means includes a recess disposed below a portion of the tube means for containing magnetic means of the type for being rotated by a magnetic stirring device for tumbling within the recess. Vibration distributing means transfers and distributes the agitation of the magnetic means throughout the entire tube means.

FIGURES IN THE DRAWINGS

Other advantages of the present invention will be readily appreciated as the same becomes better understood by reference to the following detailed description when considered in connection with the accompanying drawings wherein.

DETAILED DESCRIPTION OF THE INVENTION

Figure 1:
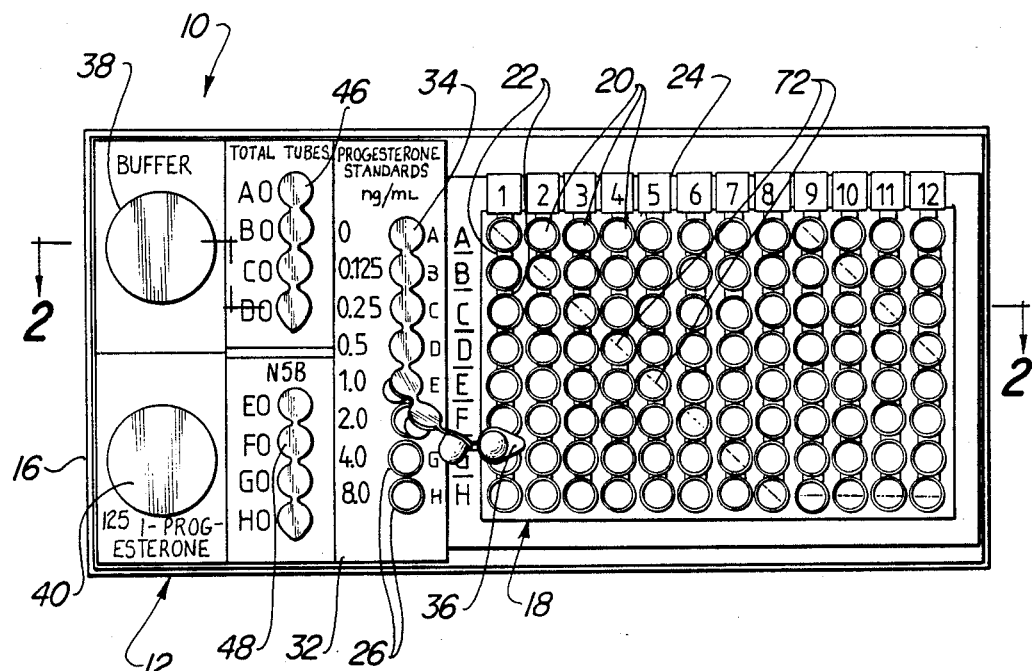
FIG. 1 is plan view of a diagnostic device constructed in accordance with the present invention.

A diagnostic device constructed in accordance with the present invention is generally shown at 10 in the Figures.

The diagnostic device 10 is in the form of a kit for assaying unknown constituent concentrations of a sample. Such constituents could consist of a hormone in a blood sample, an enzyme in a tissue culture sample, or any other constituent in biological solutions. The kit could further be adapted for assaying constituents in nonbiological solutions. The kit is specifically adapted for use in an IA system.

The device 10 includes a housing generally shown at 12 for containing the components of the device 10. The housing 12 includes a base 14 and side walls 16. The housing 12 is in the form of a container box and can be made from various materials, such as cardboard or plastic. A top portion (not shown) can be used to cover the kit for storage and shipping purposes.

The device 10 includes tube means in the form of a microtiter plate generally indicated at 18 disposed within the housing 12. The microtiter plate 18 includes a plurality of rows of wells 20 for receiving and containing a sample including the constituent to be assayed. Each row of wells 20 includes a predetermined number of wells 20 spaced a predetermined distance apart. Each of the wells 20 are interconnected to the adjacent wells 20 in row by a bridging portion 22. The plate 18 is of the type such that each row of wells 20 can be removed from an outer shell 24 of the plate 18. The outer shell 24 supports and surrounds the rows of wells 20.

The device 10 includes means for transferring samples of known quantity of the constituent to a row of wells 20 in a single step. This standard means is disposed within the housing 12 and includes a predetermined number of standard tubes 26, each of the tubes 26 containing a known concentration of the analyte schematically shown at 27. Each of the tubes 26 is spaced a predetermined distance apart equal to a predetermined distance between each of the wells 20 whereby a single pipettor, generally shown at 28 in FIGS. 3 and 4, can transfer the standards from the entire row of standard tubes 26 to a single row of wells 20 in a single transfer step.

Figure 3:
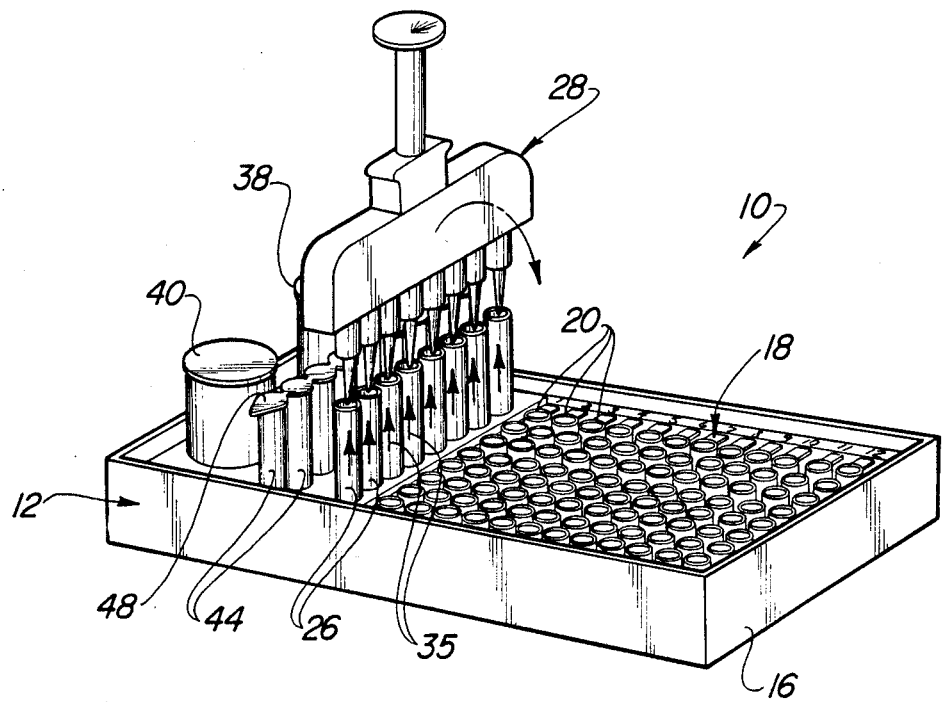
FIG. 3 is a perspective view of the subject invention and a pipettor positioned for removing a sample from the standard curve tubes thereof.
Figure 4:
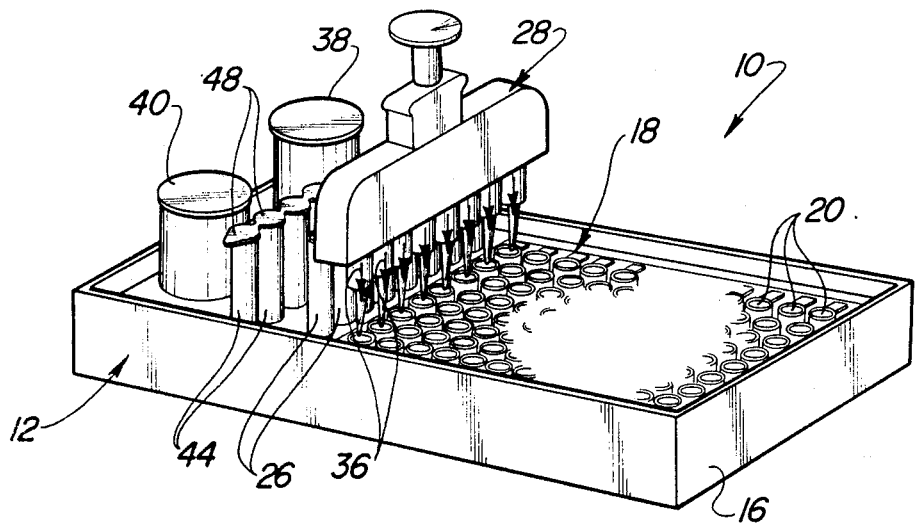
FIG. 4 is a perspective view of the present invention and the aforementioned pipettor transferring the standard solutions to a row of wells.

More specifically, each of the tubes 26 is fixedly retained within a recess 30 in a support member 32 contained within the housing 12. A plurality of interconnected plugs 34 close and perfect a seal about the open ends of the tubes 26. As shown in FIG. 1, the end plug 34 includes a tab 36 which can be gripped to consecutively remove each of the plugs 34 from the tubes 26. Since the tubes 26 are fixedly retained within the recess 30, the plugs 34 can be easily and quickly removed without disrupting the tubes 26 and pulling them from the support 32. As shown in FIG. 3, a single pipettor 28 can remove an aliquot from each of the tubes 24 in a single step, is indicated by the arrows 35 in FIG. 3. The pipettor 28 can then be directly positioned over the adjacent row of wells 20 and the aliquants can be ejected into the wells 20 as shown by the arrows 36. The present invention thereby provides a means for transferring a plurality of standards in a single step. For various kits for various diagnostic procedures, the tubes 24 would contain the corresponding various analytes to construct a standard curve for measuring analytes of unknown concentration in samples.

The device 10 further includes a buffer container 38 and a container 40 for containing radioactive or enzyme-labeled constituent. As shown in FIG. 1, the radioactive constituent is an iodinated progesterone derivative. As discussed above, various other types of radioactively or otherwise labeled constituents can be used depending upon the constituent that is assayed. The present invention shown would be specifically used for IA determinations of progesterone levels in a sample, such as a blood or tissue culture sample.

The device can also include tubes containing the amount of radioactive material added to all array wells 42 and tubes 44 used for the determination of nonspecific binding in the assay system. Tubes 42 and 44 can include plugs 46 and 48 respectively for sealing the open ends of the tubes 46,48 in a similar fashion to plugs 34.

Figure 2:
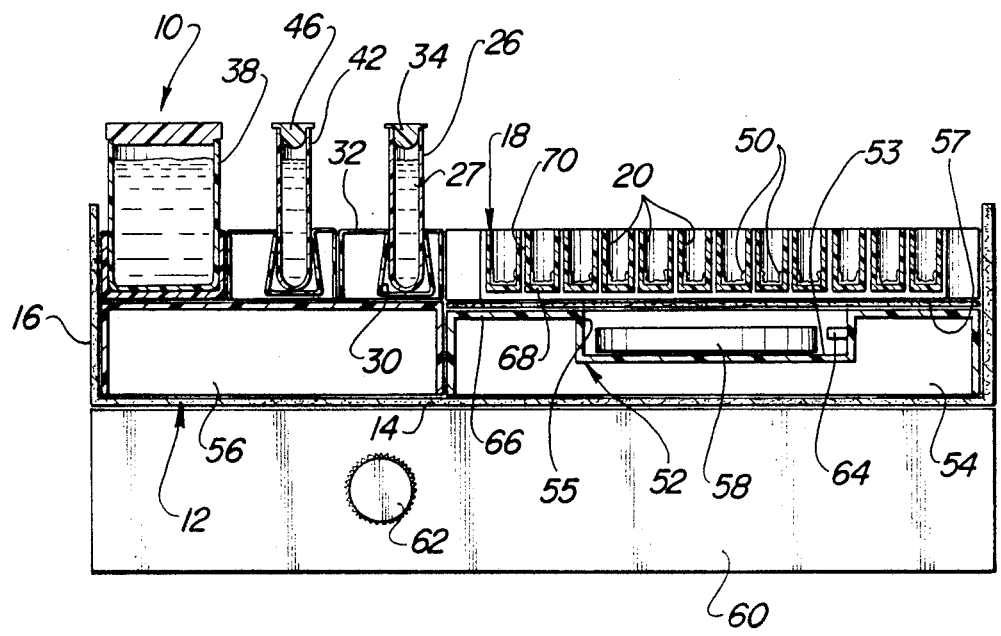
FIG. 2 is a cross section taken substantially along lines 2—2 of FIG. 1.

As shown in detail in FIG. 2, the preferred embodiment of the present invention includes antibody 50 adhered to the inner wall surfaces of the wells 20. During the assay procedure, the various chemicals, samples, iodinated tracers, or standards are transferred to the tubes. Generally, the tubes contain sample and radiolabeled tracer or standard and radiolabeled tracer. Once the samples are disposed in the wells, the samples must be incubated while agitated. The device 10 includes mixing means disposed within the housing 12 and below the microtiter plate 18 for agitating the wells 20 and mixing the samples contained therein. More specifically, the mixing means includes a recess 52 within a microtiter plate support 54, the microtiter plate 54 being contained within the housing 12 adjacent a support 56 which supports the tubes 24,38,40,42,44. The recess 52 is adapted to contain a magnetic stirring rod 58 of the type for being rotated by a magnetic stirring device 60. The magnetic stirring device 60 is of the type for containing a magnetic stirring actuator therein controlled by a control knob 62. Increasing the rotation of the magnetic actuator (not shown) by turning the control knob 62 actuates increased speed of rotation of the magnetic bar 58 within the recess 52. The device 10 includes a projection 64 which disrupts the spinning of bar 58, causing the bar 58 to tumble within the recess 52. The depth of the recess 52 is critical because the bar 58 will tumble and cause greater agitation when the recess 52 is formed to a greater depth. The recess 52 includes a flat floor portion 53 and a wall 55 extending completely thereabout. Likewise, if the recess 52 is shallow, the bar 58 will be prevented from violent tumbling.

A board member 66 is disposed between the microtiter plate 18 and the support 54, the board member 66 extending completely over the recess 52 to function as a vibration distributing means for transferring and distributing the agitation of the tumbling bar 58 throughout the entire microtiter plate 18. The board member 66 is disposed over the recess 52 and extends under the entire undersurface 57 of the microtiter plate 18.

In operation, once the samples and standards are disposed within the wells 20, the magnetic stirring device 60 is turned on and the bar 58 is caused to rotate. The projection 64 prevents perfect rotation of the magnetic bar 58 and causes it to tumble. The tumbling bar 58 contacts the board 60 and causes it to vibrate. The board 66 translates the vibration throughout the entire microtiter plate 18 thereby mixing the samples within the wells 20. Controlling the magnetic stirring device controls the extent of tumbling of the bar 58 and thusly controls the extent of mixing within the wells 20.

Alternatively, the recess 52 may not include a projection 64. With this alternative structure, the magnetic stirring device 60 is turned on rapidly to a high power causing the bar 58 to tumble rather than spin perfectly. Again, the extent of actuation of the magnetic stirring device 60 will control the amount of tumbling of the bar 58 and the extent of mixing within the wells 20.

As stated above, the microtiter plate 18 includes an outer casing 24 and removable rows of wells 20 connected to the outer casing 24. The device 10 includes means on each row of wells 20 for indicating the position of the row of wells 20 relative to the other rows of wells 20. More specifically, each of the wells 20 includes a base portion 68 and side walls 70, as indicated in FIG. 2. The means for indicating the relative row position of a row of wells 20 includes a translucent marking 72 on a base portion 68 of at least one of the wells 20 at a different position in each of the rows. Alternatively, the marking can be on the top rim of he wells. The markings 72 of the wells 20 together form a predetermined pattern wherein each of the markings 72 indicates a known position of the row of wells 20 relative to the other rows. As shown in FIG. 1, the markings 72 indicate a diagonal line for the first eight rows of wells and then a diagonal line in combination with a straight line in the last four rows of wells. If three rows of wells 20 were intentionally or inadvertently removed from the device 10 the position and orientation of those rows would be immediately indicated by the markings 72 in relation to the predetermined pattern of the markings. Hence, this aspect of the invention provides means for indicating and identifying the relative positions of the rows of wells 20 on the outer casing 24.

The present invention provides several elements which in combination or alone greatly increase the efficiency and ease of performing and perfecting an IA or various other types of assays in which these elements can be adapted The various elements in combination as the device 10 provide a novel and useful assay mechanism which function together and synergistically to provide an improved IA diagnostic kit.

What is claimed:

1. A diagnostic device (10) for assaying unknown constituent concentrations in a sample, said device, (10) comprising the combination of: housing means (12) for containing said device (10); tube means (18) disposed within said housing means (12) and including a plurality of rows of wells (20) for receiving and containing a sample including a constituent to be assayed, each of said rows including a predetermined number of said wells (20) spaced a predetermined distance apart; and agitating means disposed within said housing means (12) and below said tube means for agitating said wells (20) and mixing the sample contained therein, said agitating means including a recess (52) disposed below a portion of said tube means (18) for containing a magnetic rod (58) of the type for being rotated by a magnetic stirring device (60) for tumbling within said recess (52), and vibration distribution means for transferring and distributing the agitation of the magnetic rod throughout said entire tube means (18), wherein said agitating means includes rod spin disrupting means (64) disposed within said recess (52) for disrupting the spin of the spinning magnetic rod (58) within said recess (52) so that the rod (58) agitates said vibration distribution means (66).

2. A device as set forth in claim 1 wherein said tube means (18) includes an outer casing (24) and connecting means (22) for connecting together each of said wells (20) in a row to each other, each of said rows of wells (20) being removably connected to said outer casing (24), said device (10) further including well row indicating means on each row of said wells (20) for indicating the position of each row of said wells (20) relative to the other rows of said wells (20).

3. A device as set forth in claim 2 wherein each of said wells (20) includes a base portion (68) and an annular side wall (70) extending thereabout, said well row indicating means including a marking (72) on said base portion (68) of one of said wells (20) at a different position in each of said rows, said markings (72) of said wells (20) together forming a predetermined pattern wherein each of said markings (72) indicates a known position of said row of said wells (20) relative to the other of said rows.

4. A device as set forth in claim 1 wherein said housing means (12) includes a platform insert (54) contained therein and including said recess (52) for containing a magnetic rod (58) therein, said recess (52) including a substantially flat floor portion (53) and wall (55) extending completely thereabout, said tube means (18) including an undersurface (57), said vibration distributing means (66) being disposed over said recess (52) and extending beneath said entire understructure (57) of said tube means (18).

5. A device as set forth in claim 4 wherein said vibration distributing means includes a board member (66) disposed over said platform insert (54) and below said tube means (18).

6. A device as set forth in claim 1 wherein said rod spin disrupting means includes a projection (64) extending into said recess (52) for contacting the rod (58) and disrupting the spinning motion of the rod (58).

7. A device as set forth in claim 1 further including standard means disposed within said housing means and containing a plurality of standard solutions for being dispensed into a row of said wells (20) said standard means including a row of said predetermined number of standard tubes (24) each of said tubes (24) containing a known quantity of the constituent (26) and each of said tubes (24) being spaced said predetermined distance apart as said wells (20) whereby a single pipettor (28) can transfer the standards from said entire row of standard tubes (24) to a single row of said wells (20) in a single transfer step.

8. A device as set forth in claim 7 further including removable cover means (34) for covering and sealing each of said standard tubes (26).

9. A device as set forth in claim 8 wherein said cover means (34) includes a plurality of interconnected plugs (34), each of said plugs (34) being seated within a respective one of said standard tubes (26).

10. A device as set forth in claim 9 wherein said housing means (12) includes standard tube support means (32) for supporting and fixedly retaining each of said standard tubes (26) therein and preventing displacement of said standard tubes (26) during removal of said plugs (34) therefrom.

* * * * *